US007927333B2

(12) United States Patent
Gradl (10) Patent No.: US 7,927,333 B2
(45) Date of Patent: Apr. 19, 2011

(54) SYSTEM FOR THE MINIMALLY INVASIVE TREATMENT OF A BONE FRACTURE, ESPECIALLY OF A PROXIMAL HUMERAL OR FEMORAL FRACTURE

(75) Inventor: Georg Gradl, Boergerende (DE)

(73) Assignee: Intercus GmbH, Rudolstadt (DE)

( * ) Notice: Subject to any disclaimer, the term of this patent is extended or adjusted under 35 U.S.C. 154(b) by 573 days.

(21) Appl. No.: 10/576,351

(22) PCT Filed: Oct. 15, 2004

(86) PCT No.: PCT/DE2004/002312
§ 371 (c)(1),
(2), (4) Date: Feb. 21, 2007

(87) PCT Pub. No.: WO2005/037117
PCT Pub. Date: Apr. 28, 2005

(65) Prior Publication Data
US 2007/0225714 A1    Sep. 27, 2007

(30) Foreign Application Priority Data
Oct. 18, 2003   (DE) .................................. 103 48 932

(51) Int. Cl.
*A61B 17/58*   (2006.01)
*A61B 17/64*   (2006.01)
*A61B 17/86*   (2006.01)
*A61B 17/90*   (2006.01)
*A61F 2/28*    (2006.01)

(52) U.S. Cl. ......... 606/86 B; 606/86 R; 606/87; 606/96; 606/98; 606/280; 606/286; 606/300; 606/902; 606/903; 606/904; 606/905; 606/906

(58) Field of Classification Search ............ 606/60, 606/62, 64–67, 300, 86 R, 86 B, 87–89, 96, 606/98, 915, 280–286, 902–906
See application file for complete search history.

(56) References Cited

U.S. PATENT DOCUMENTS

| 3,107,666 | A  |   | 10/1963 | Cecere et al. |
| 3,939,498 | A  | * | 2/1976  | Lee et al. ............... 623/23.27 |
| 4,530,355 | A  |   | 7/1985  | Griggs |
| 4,612,920 | A  | * | 9/1986  | Lower .................... 606/66 |
| 5,429,641 | A  | * | 7/1995  | Gotfried ................ 606/67 |
| 5,498,265 | A  |   | 3/1996  | Asnis et al. |
| 6,562,042 | B2 | * | 5/2003  | Nelson .................... 606/62 |
| 2003/0040752 | A1 |   | 2/2003 | Kitchens |
| 2003/0078581 | A1 | * | 4/2003 | Frei et al. ............... 606/68 |

FOREIGN PATENT DOCUMENTS

| EP | 0 085 493    | 8/1983  |
| EP | 0 617 927    | 10/1994 |
| FR | 2572648      | 5/1986  |
| GB | 945292       | 12/1963 |
| WO | WO-89/06940  | 8/1989  |
| WO | WO-03/015650 | 2/2003  |

* cited by examiner

(Continued)

*Primary Examiner* — Eduardo C Robert
*Assistant Examiner* — Sameh Boles
(74) *Attorney, Agent, or Firm* — Jordan and Hamburg LLP (57) ABSTRACT

The invention relates to a system for the minimally invasive treatment of a bone fracture, especially of a proximal humeral or femoral fracture. The inventive system has an osteosynthesis plate having a supporting section in the cortical substance and an additional fastening section on the bone. A second linking section of the guide element and the shaft of the fixing element are configured as an axially displaceable anti-tilt slide bearing. The system has at least one anti-twist screw in the supporting section for preventing the detached bone fragment from rotation.

30 Claims, 4 Drawing Sheets

SYSTEM FOR THE MINIMALLY INVASIVE TREATMENT OF A BONE FRACTURE, ESPECIALLY OF A PROXIMAL HUMERAL OR FEMORAL FRACTURE

BACKGROUND OF THE INVENTION

The invention relates to a system for minimally invasive treatment of a fracture of a bone, in particular a proximal humeral or femoral fracture.

As is known, surgical therapy has a solid position in the treatment of bone fractures. As a rule, surgery is indicated when there is significant dislocation of fracture fragments, when dislocation of the fragments caused by the fracture cannot be corrected solely by repositioning, or in the case of multiple fragment-fractures. Basically surgical methods that have preference are those with the lowest degree of damage to the soft tissue and with the advantage of early post-surgical motion therapy. Therefore systems for minimally invasive therapy of bone fractures are of increased importance. However, suitable systems for minimally-invasive therapy are not available for every different type of fracture that occurs. In the case of the shoulder, in the past access from the outside of the upper arm has not been common because known surgical techniques involve the risk of injuring the circumflex nerve.

Using plates and screws is one of the standard procedures when treating fractures of the upper arm that involve the head end of the upper arm bone (also called the humerus). With these bone fractures, also called proximal humeral fractures, the plates and screws are inserted in the usual manner, that is, in a manner that is not minimally invasive, via a sufficiently large incision in the skin, which in adults is about 10 cm long. Muscular coat, muscles, and even the joint capsule of the shoulder joint must be transected in order to attach the plate to the humerus using the screws. Fracture healing is satisfactory with this method. The large surgical access imposes major strain on the shoulder, however. Since the shoulder joint does not have much of a bony guide and a thick covering of musculature surrounds the shoulder, interventions into the soft tissue of the shoulder that are required for placing the plates and screws are generally associated with substantial post-operative movement limitations.

For treating proximal humeral fractures, so-called intramedullary nailing has become known as a particularly gentle method for avoiding damage to soft tissue. In this case, after the bone marrow cavity has been opened, thin nails are inserted, via a small incision just above the elbow, in the medullary space up to the upper end of the humerus past the site of the fracture. However, this method is only suitable for a few very simple types of fractures. In fractures with a plurality of fragments, the nails migrate upward through the open bone sites in the fracture area and cause problems in the joint.

A system called the "dynamic hip screw" has become known for treating fractures that affect the hip-end of the upper leg bone (also called a proximal femur fracture). This system is used to join a bone fragment to the non-fractured part of the bone. The dynamic hip screw system has a screw that, after creating a corresponding bore, is screwed into the bone fragment. The screw is dimensioned such that its entire length is received in the bore. The free end of this screw is fixed using a plate that is screwed to the bone. At its one end, the plate has a tube-shaped section arranged at an angle to the longitudinal axis of the plate. Prior to fastening the plate to the bone, this section is guided into the bore of the bone in order to receive and fix the free end of the aforesaid screw. However, the dynamic hip screw system cannot be used in a minimally invasive manner. It is also not suited for treating humeral fractures.

A system for minimally invasive treatment of a fracture of a bone is also known in accordance with U.S. Pat. No. 5,429,641. In this case, "long screws" are inserted via a connecting section in a sleeve in the bone. The system of "long screws" is constructed anti-tilt and axially displaceable, but only while being screwed into the bone. It is disadvantageous that after the screws are set it is a rigid connection that comprises tension and that does not permit axial displacement after installation.

SUMMARY OF THE INVENTION

The object of the present invention is therefore to suggest a system for minimally invasive treatment of bone fractures that can be used to attain good stability in the area of the fracture and that simultaneously causes only limited damage to soft tissue.

This object is attained using a system for minimally invasive treatment of a bone fracture, in particular a proximal humeral or femoral fracture, including an osteosynthetic plate that has a support section that can be positioned with a support surface against the bone adjacent to the fracture and a fastening section for fixing the osteosynthetic plate to the bone, a fixation element for fixing in a fragment of the bone that was dislodged by the fracture, and a guide element that can be fixed via a first connecting section on the osteosynthetic plate and that has a second connecting section for guiding the fixation element, whereby the support section of the osteosynthetic plate has at least a first recess and the fixation element and the guide element can be inserted into the bone through the first recess.

Using this configuration makes it possible to stabilize fractures, in particular sub-capital humeral and femoral fractures, using an osteosynthetic plate in a minimally invasive manner and to fix the bone fragments in their position relative to one another.

The inventive osteosynthetic plate can be placed against the bone through a small incision that, in the case of sub-capital humeral fracture, is made below the head of the humerus, and can then be urged upward along the bone so that it scrapes the musculature until the support section is adjacent to the fracture to be stabilized. After the osteosynthetic plate has been fixed to the bone in this position via the fastening section, and after another small incision is made in the skin and a bore has been made in the bone, the fixation element can be inserted through the first recess into the bone and fixed in the bone fragment that was created by the fracture. The guide element that was also placed through the first recess is connected via its first connecting section to the osteosynthetic plate and via its second connecting section to the fixation element, this guiding the latter into the fracture in a stabilizing manner. The inventive system can be used to treat complicated fractures in a minimally invasive manner, as well, without having to damage a large amount of soft tissue. This is particularly advantageous for proximal humeral fractures, because neither the musculature that supports the shoulder nor the joint capsule undergo substantial damage. Post-surgical healing is consequently accelerated. Limitations to shoulder movements are substantially reduced.

In accordance with one advantageous embodiment of the invention it is provided that the first recess in the support section and the guide element are embodied such that a longitudinal axis of the guide element and a surface area running on a tangential to the side of the osteosynthetic plate facing the bone are at an angle of between 50° and 70°, in particular between 55° and 65°. An osteosynthetic plate embodied in such a manner is particularly suitable for proximal humeral fractures.

Undesired movements by the guide element are countered in that provided on the osteosynthetic plate and/or the guide element are fastening means that hold the guide element axially fast in both directions after placement into the osteosynthetic plate.

Handling is simplified in that alignment means are provided that can be used to adjust and/or control the rotational position of the guide element relative to the osteosynthetic plate. This is particularly advantageous when an additional bone splinter fixation element is to be connected to the guide element, as is described in greater detail in the following.

In accordance with one advantageous embodiment, the fastening means include a groove embodied in the first recess of the support section and a corresponding nose embodied on the guide element, which can be inserted into the groove.

Provided in the groove is a stop that is for positioning at the nose and that limits a rotational movement of the guide element. This is how the rotational position of the guide element relative to the osteosynthetic plate can be adjusted and/or checked.

Alternatively, the fastening means can include a male thread embodied on the first connecting section of the guide element and a female thread that is embodied in the first recess and that can be caused to engage with the male thread.

Good guidance of the fixation element is attained in that the second connecting section of the guide element is embodied as a seat in which a shaft of the fixation element is received in an anti-tilt and axially displaceable manner. Due to the axial displaceability, settling that occurs at the bone fissure during the course of healing can be compensated. Consequently, the fixation element can also be characterized as a sliding fixation element or if the fixation element is embodied as a screw can be characterized as a slide bolt.

In accordance with one embodiment of the invention, the shaft of the fixation element has catch surfaces that hold the fixation element rotationally fast in the seat. This enables the fixation element to be screwed into the bone fragment by means of a tool, in some circumstances also using the guide element. At the same time, this attains rotational fixation between guide element and fixation element. Alternatively, the shaft of the fixation element can also be rotationally held in the seat.

In accordance with one particularly advantageous embodiment of the invention, a bone splinter fixation element is provided that can be fixed in or to the guide element, in particular in a transverse bore provided therein. This configuration is in particular advantageous when, as is frequently the case, three or even more bone fragments have occurred due to the fracture. Using the bond splinter fixation element, another bone fragment can then be held to the osteosynthetic plate and thus bone healing can be accelerated.

In accordance with one further development of this inventive thought, the transverse bore is arranged in the guide element such that a longitudinal axis of the longitudinal bone splinter fixation element and a longitudinal axis of the guide element create an angle of between 60° and 100°, in particular between 70° and 90°. In this case the inventive system is particularly suitable for humeral fractures in which the greater tuberosity fragment has been separated.

Not only is it possible to use the bone splinter fixation element to hold this splintered fragment, it is also possible to exert a pressure in the desired direction that is advantageous for rapid bone formation.

Fixation of a splintered bone fragment or bone splinter is made easier when the bone splinter fixation element is embodied as a screw that has a pressure body with claws.

Another improvement is attained in that means are provided for preventing rotation of the dislodged bone fragment. Preferably provided for this is an anti-rotation screw that has a head and that can be placed into the dislodged bone fragment through at least a second recess in the support section.

Rotational movements by the bone fragment are reliably prevented due to the fixation by the fixation element, which is held on the osteosynthetic plate via the guide element, and the anti-rotation screw.

Fixation of the anti-rotation screw to the osteosynthetic plate is enhanced in that the second recess has a female thread and the anti-rotation screw has a corresponding male thread on its head.

This configuration achieves greater stability, in particular tilting of the anti-rotation screw is prevented.

For inserting the inventive system in a minimally invasive manner, the latter has an aiming device that is detachably connected to the osteosynthetic plate. This aiming device makes it possible in a simple and minimally invasive manner to bring the osteosynthetic plate to the desired position, attach it to the bone, and insert the fixation element, the guide element, the anti-rotation screw, and the bone splinter fixation element into the bone.

Adding bores to the bones and assembling the individual elements is facilitated in that the aiming device has target bores that align with the recesses in the osteosynthetic plate.

It has been demonstrated that it is also possible to perform minimally invasive treatment of bone fractures using the system without employing the osteosynthetic plate provided the cortical bone of the bone is sufficiently strong.

In accordance with the invention, in this case the guide element is screwed directly to the cortical bone. The fixation element that is slidingly borne in or on the guide element, as already described, is fastened to the fractured piece of bone that has broken off. In order to preclude this fractured piece from rotating, at least one anti-rotation screw can be added in the support section of the bone in the cortical bone such that it reaches into the soft part of the fragment of the bone that was dislodged by the fracture. In this case, as well, as already described in the foregoing, at least one bone splinter fixation element can be fastened in or to the guide element.

The fixation element is fastened by screwing it directly into the osteosynthetic plate or even into the cortical bone, then the first connecting section at the end is preferably shaped such that an aiming device can be positioned at the bone splinter fixation element for the bore alignment thereof such that after boring the bone splinter fixation element can be fastened in or to the guide element with no problem.

Corresponding to the surgical requirements, guide elements can also be used in which or to which a plurality of bone splinter fixation elements can be fastened.

The bore direction for the anti-rotation screws when using an osteosynthetic plate can also be established using known bore templates.

In another embodiment, the connecting section is configured between fixation element and guide element such that sliding is no problem, but a limiting stop, such as for instance a snap ring, a pin, a border, or the like on the connecting section of the guide element or shaft of the fixation element prevents the two parts from decoupling because it engages in a circumferential groove.

In this case it is another advantage that the axial displacement when sliding, e.g. due to the width of the groove, can be limited to a value specified in advance. It has been demonstrated that axial displacement in general up to 10 mm is sufficient for a fracture.

In another embodiment, the shaft of the fixation element is borne sliding, anti-tilt, and axially displaceable in a seat of the guide element. In another embodiment, the shaft of the fixation element is configured such that it encompasses the second connecting section of the guide element from outside. In this case, as well, it is borne sliding, anti-tilt, and axially displaceable. A limit is also possible.

It is particularly advantageous when the slidingly borne connection is configured such that it is possible for the fixation element to rotate about the axis.

In these embodiments, at the end of the shaft of the fixation element a fixation recess is arranged centrically for receiving a rotational tool. This fixation recess can have the form of a female thread for receiving a screw or another form for receiving a nonpositive-fit connecting element so that a forced rotation of the fixation element is possible to screw it into the fractured part of the bone. In this case, a rotational tool through-bore for receiving the rotational tool is arranged axially in the guide element.

Additional goals, features, and application options of the present invention result from the following description of the exemplary embodiment using the drawings. All of the described and/or graphically illustrated features, alone or in any desired combination, constitute the subject of the invention, regardless of how they are summarized in individual claims or references to previous claims.

BRIEF DESCRIPTION OF THE DRAWINGS

Accompanying the specification are figures which assist in illustrating the embodiments of the invention, in which.

DETAILED DESCRIPTION OF THE INVENTION

The figures illustrate a system for minimally invasive treatment of a bone fracture. The inventive system is fundamentally suitable for treating different bone fractures. However, it is particularly suitable for proximal humeral or femoral fractures, that is, for those bone fractures at the end of the humerus or femur that is closest to the body. The figures and the following description explain the invention in an exemplary manner using the illustrated system for treating a proximal humeral fracture without limiting the invention thereto.

Figures 1, 2A, 2B:
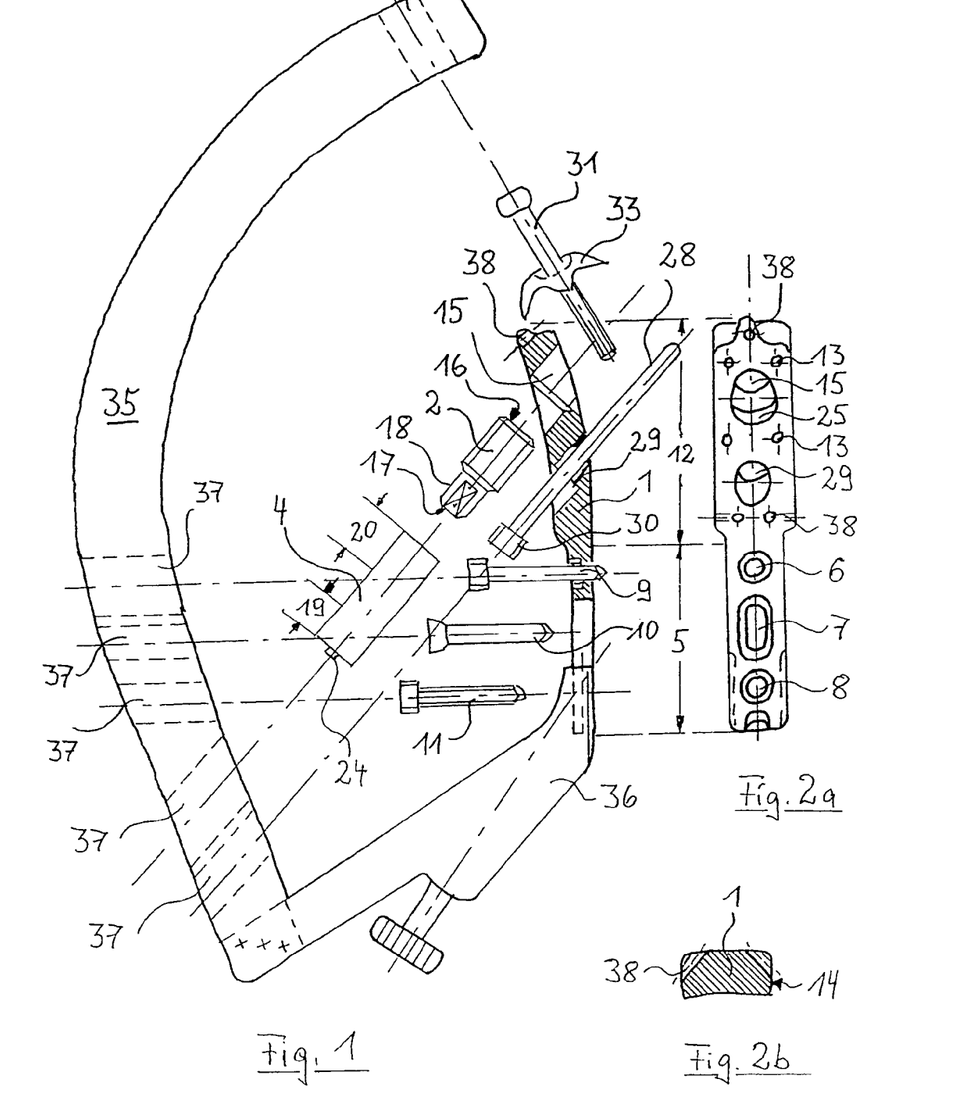
FIG. 1 is a side view, partially in section, of the inventive system for minimally invasive treatment of a bone fracture.
FIG. 2a is a top view of the inventive osteosynthetic plate.
FIG. 2b is a section through the osteosynthetic plate illustrated in FIG. 2a, transverse to its longitudinal direction.
Figures 3, 4, 5, 6:
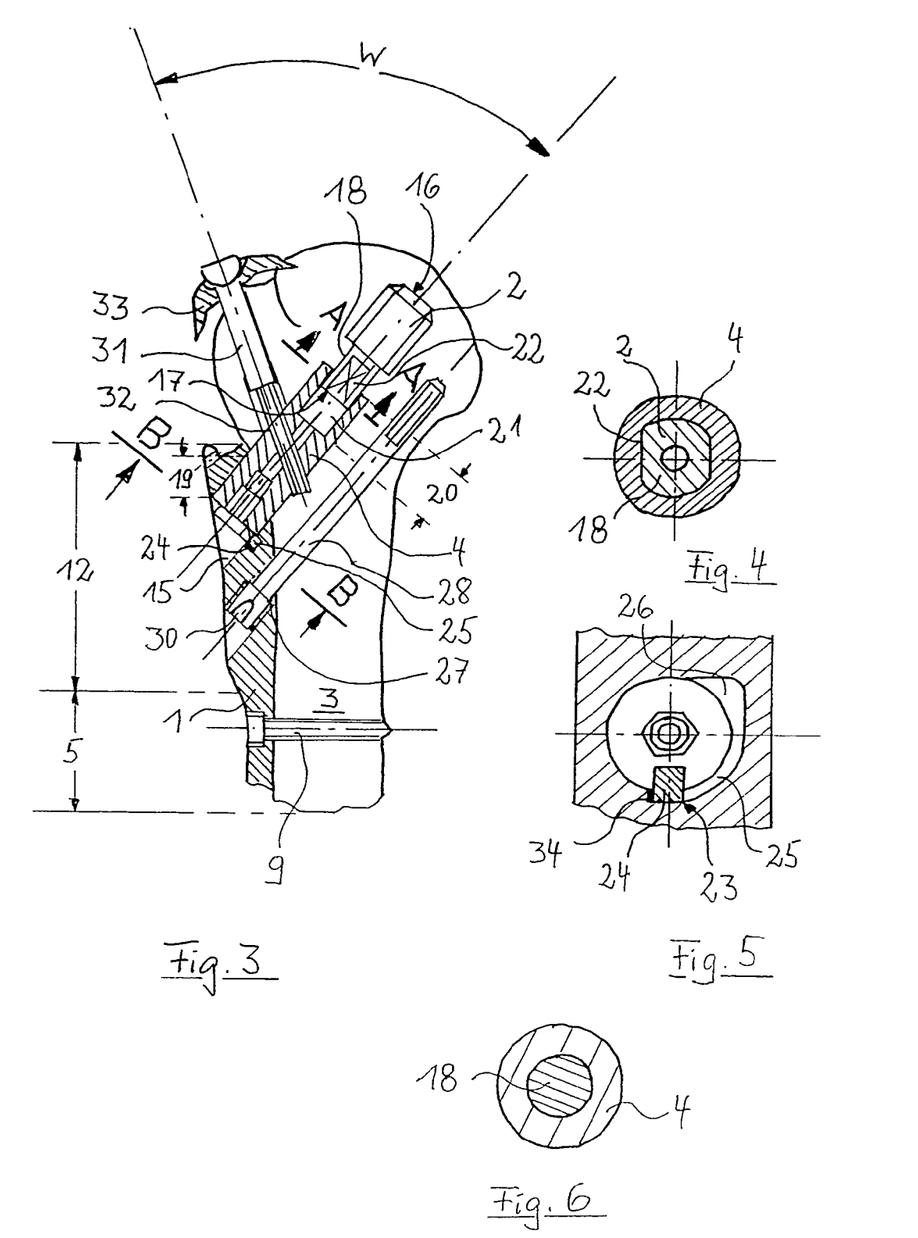
FIG. 3 is a sectional depiction of an inventive system in its installed position.
FIG. 4 is a section through the inventive system along the line A-A in FIG. 3.
FIG. 5 is a section through an inventive system approximately along the line B-B in FIG. 3, but in a slightly modified embodiment.
FIG. 6 is a sectional depiction along the line A-A through an alternative embodiment.

As can be seen from FIGS. 1 and 3, the system is embodied as a kit and contains an osteosynthetic plate 1, a fixation element for fixing in a fragment of the bone 3 that has been dislodged by the fracture, and a guide element 4 for the fixation element 2.

The longitudinally embodied rigid osteosynthetic plate 1 has a fastening section 5 via which the osteosynthetic plate 1 can be attached to the intact shaft of the bone 3. For this purpose, three through-holes 6, 7, 8 are arranged in a line in the approximately rectangular fastening section 5. These make it possible to add means for fastening the osteosynthetic plate 1 to the bone 3. In the embodiment illustrated, the through-holes 6 and 8 are embodied in a circular shape, while the through-hole 7 is an oblong hole that extends along the longitudinal axis of the osteosynthetic plate. Three cortical bone screws are provided as means for fastening the osteosynthetic plate. The cortical bone screw 10 intended for the through-hole 7 embodied as an oblong hole has a screw head that has been rounded off and that is also known as a spherical head. In contrast, the cortical bone screws 9 and 10 have a cylindrical screw head that is provided with a male thread. A female thread that corresponds to the male thread of the heads of the cortical bone screws 9 and 11 is provided in the through-holes 6 and 8 of the osteosynthetic plate 1 into which the heads of the cortical bone screws 9 and 11 can be turned until they are stopped.

Using this configuration, the cortical bone screws 9 and 11 are held in a stable and secure manner in every direction to the osteosynthetic plate. Each cortical bone screw 9 and 11 has a thread on its shaft that is suitable for screwing into the corresponding bores provided in the bone 3.

Above the fastening section 5, the osteosynthetic plate 1 has a support section 12 that in the illustrated embodiment is somewhat wider than the fastening section 5. Both sections can be embodied differently, in particular with identical widths. In addition, placement of the osteosynthetic plate 1 under a muscle is facilitated in that the free end of the support section 12 has a slide area with a smaller thickness and is embodied running flat to the bone (not shown).

The support section 12 likewise has an approximately rectangular basic form. It has (four) bores 13, each of which passes through the front side illustrated in FIG. 2a to the side of the osteosynthetic plate 1 that faces the bone. The bores 13 make it possible to initially temporarily fix the fracture in order to subsequently use the fixation element 2 in the fragment of bone 3 separated by the fracture. This can occur for instance using so-called Kirschner wires that are inserted through the bores 13 into the bone 3. In addition, after the Kirschner wires have been removed, if necessary additional screws (not shown) can be inserted through the bores 13 into the bone 3 to stabilize the fracture. For this, the bores 12 have a female thread into which the screws can be screwed, angle-stable, via a male thread provided at their head.

Moreover, the support section 13 has (three) through-holes 38 arranged on an incline that each pass through from the front side illustrated in FIG. 2a to the lateral surface 14. This can be seen in FIG. 2b, which illustrates a cross-section through the support section 12 in the area of the lower two through-holes 38. If the osteosynthetic plate 1 is to be used in an open surgery, that is, a surgery that is not minimally invasive, the through-holes 38 can be used to fix fracture fragments (in particular the greater tuberosity fragment) with sutures.

FIG. 2b furthermore illustrates that the bottom of the osteosynthetic plate 1 is curved in a direction transverse to its longitudinal axis, this improving the position at the bone 3. The support section 12 of the osteosynthetic plate 1 has a slightly convex shape that arches in the direction of its longitudinal axis. This improves the contact with the expanded head of the bone 3.

Provided in the support section 12 is a first recess 15 that extends through the osteosynthetic plate 1. The first recess 15 and the fixation element 2, described in greater detail below, and the guide element 4 are dimensioned such that the fixation element 2 and the guide element 4 can be inserted through the first recess 15, starting in the position illustrated in FIG. 1, into the bone 3 and/or a bore to be inserted therein in advance and brought into the position illustrated in FIG. 3. Consequently the exterior diameter of the fixation element 2 and of the guide element 4 is somewhat smaller than the interior diameter of the first recess 15. The first recess 15 in the support section 12 and the guide element 4 are embodied such that a longitudinal axis of the guide element 4 and an imaginary tangent to the side of the osteosynthetic plate that faces the bone 3 form an angle of 50° to 70°, in particular 55° to 65°. The free end of the guide element 4 faces away from the fastening section 5. This angled arrangement is attained in that the first recess 15 extends on an incline through the support section 12.

The fixation element 2 is embodied as a screw and has on its forward end 16 an appropriate self-cutting thread for screwing into the bone 3. Embodied at the rear end 17 of the fixation element 2 is a shaft 18 via which it can be connected to the guide element 4. The shaft 18 is embodied hollow in the illustrated embodiment.

The guide element 4 guides the fixation element 2. For this, the guide element 4 has a first connecting section 19 via which it can be fixed to the osteosynthetic plate 1. A seat 21 for the shaft 18 of the fixation element 2 is provided in the second connecting section 20 embodied on the opposing free end of the guide element 4. The shaft 18 and the seat 21 are embodied such that the fixation element 2 is received anti-tilt and axially displaceable in the guide element 4. Due to the displaceability of the fixation element 2, displacement in the area of the fracture that occur during the healing process can be compensated by sliding. Consequently, the fixation element 2 embodied as a screw can also be called a slide bolt in the illustrated embodiment.

In the direction of rotation the fixation element 2 in the illustrated embodiment is securely held in the seat 21. For this, corresponding catch surfaces 22 are embodied on the shaft 18 and in the seat 21 as depicted in FIGS. 3 and 4. This configuration makes it possible first of all to screw in the fixation element 2 while rotating the guide element 4 into the bone 3. At the same time, rotational securing is produced in this manner that prevents rotation between fixation element 2 and guide element 4. In the illustrated embodiment, two parallel opposing catch surfaces 22 are provided on the exterior of the otherwise cylindrical shaft 18. However, a different non-circular corresponding cross-sectional shape can be used for the shaft 18 and the seat 21, for instance a square or hexagon.

FIG. 6, which provides a sectional guide as in FIG. 4, depicts the section through the shaft 18 and the seat 21 of an alternative embodiment. In this case, the fixation element 2 and the guide element 4 are not embodied rotation-fast relative to one another. This is attained by a sectionally circular embodiment of shaft 18 and seat 21 that does not have any catch surfaces. This configuration makes it possible to unscrew the guide element during surgery, which can make assembly easier.

The guide element 4, having a smooth cylindrical exterior shape, is embodied continuous and can therefore also be called a slide. The exterior diameter of the guide element 4 and the first recess 15 in the osteosynthetic plate 1 is dimensioned such that the guide element 4 is held in the osteosynthetic plate 1 in an anti-tilt and precise-fitting manner. The system can be adapted to different size bones using different lengths of the guide element 4.

Movements by the guide element 3 are undesirable after the osteosynthetic plate 1 has been put in place. Therefore fastening means 23 are provided that hold the guide element 4 axially fast in both directions. In the exemplary embodiment depicted, the fastening means 23 are formed by the projection in the form of a nose 24 of the guide element 4, which projects laterally on the guide element 4 and can be caused to engage with a groove 25 in the osteosynthetic plate 1. The groove 25 extends transverse, in particular perpendicular, to the longitudinal axis of the guide element 4 and is arranged in the area of the first recess 15. FIG. 5 illustrates this. In accordance with FIG. 3, the groove 25 runs to the top of the osteosynthetic plate 1. This is how the nose 24 can be easily inserted into the groove 25. Alternatively or in addition, as FIG. 5 depicts, the groove 25 can have an expanded section 26 that is open to the outside, via which the nose 24 can be introduced into the groove 25.

Furthermore, in accordance with the invention means 27 for preventing rotation of the bone fragment displaced by the fracture are also provided. In the embodiment depicted, these include an anti-rotation screw 28 that has a head and that can be placed into the dislodged fragment of the bone using at least a second recess 29 embodied in the support section 12 of the osteosynthetic plate 1. In the embodiment depicted, the second recess 29 is arranged such that the anti-rotation screw 28 extends parallel to the longitudinal axis of the guide element 4, specifically on the side of the first recess 15 that faces the fastening section 5. Alternatively and in contrast to the depiction, the anti-rotation screw 28 and the guide element 4 can also be arranged at an angle to one another (especially 10° to 49°), which in some circumstances enables even better fracture stabilization.

Like the cortical bone screws 9 and 11, the anti-rotation screw 28 has an expanded head 30 with a male thread that can be screwed into a corresponding female thread provided in the second recess 29 until it reaches a stop. The anti-rotation screw 28 is embodied as a shaft screw that is provided with a thread suitable for screwing into the bone 3, not over the entire length of the screw shaft, but rather on the end opposing the head 30.

Not shown are embodiments in which a plurality of anti-rotation screws are arranged and used in the fastening section.

The inventive system furthermore provides a bone splinter fixation element 31. However, it does not necessarily have to be used. It is advantageous in particular when the fracture has led to three or more bone fragments. In the embodiment depicted for treating a proximal humeral fracture, the bone splinter fixation element 31 can securely fix the greater tuberosity fragment. This occurs in that the bone splinter fixation element 31, which in the embodiment depicted is embodied as a screw, is inserted into a transverse bore 32 embodied in the guide element 4 and held thereby. The bone splinter fixation element 31 has a longitudinal shaft that is provided on its lower end with a thread that can be screwed into a female thread provided in the transverse bore 32. The transverse bore 32 and thus the longitudinal axis of the bone splinter fixation screw 31 on the one hand and the longitudinal axis of the guide element 4 on the other hand create an angle between 60° and 100°, especially between 70° and 90°.

In this, the longitudinal axis of the bone splinter fixation screw 31 inclines away from the osteosynthetic plate 1 when the angle W is less than 90° and towards the osteosynthetic plate 1 when the angle W is greater than 90°.

In the embodiment depicted, the bone splinter fixation element 31 is embodied as a claw bolt that has under its expanded screw head a pressure body 33 having a plurality of claws.

In order to be able to screw the bone splinter fixation element 31 into the transverse bore 32 without any problems, it is necessary to first bring the guide element 4 into the correct rotational position, since otherwise the bone splinter fixation element 31 would miss the opening in the transverse bore 32. Used for this are alignment means through which the rotational position of the guide element 4 can be adjusted and/or controlled relative to the osteosynthetic plate 1. In the embodiment depicted, the correct positioning of the guide element 4 is assured in that a stop 34 for positioning at the nose 24 is provided in the nose 25 and limits the rotational movement of the guide element 4.

Thus, in that the nose 24 is moved until it is positioned against the stop 34, it is possible to assure correct and precise alignment of the guide element 4.

FIG. 1 also depicts a target device 35 that makes it possible to position the inventive system and attach it to the bone in a minimally invasive manner. The target device 35 is detachably connected, but connected play-free, to the osteosynthetic plate 1 via a clamping section 36. A dovetail guide can be provided for this between target device 35 and osteosynthetic plate 1. The target guide 35 makes it possible to provide the necessary bores in the bone 3 and then to mount the other elements of the inventive system on the bone 3. The target device 35 is particularly important in the minimally invasive treatment since the other system components cannot be mounted under direct visual monitoring. Target bores 37 provided in the target device 35 are aligned with the recesses of the osteosynthetic plate.

These bores 37 are used in a known manner to guide drills in order to be able to add bores to the bones 3. Likewise, the guide can be used to deliberately place the various elements of the inventive system at their respective intended positions.

Figure 7:
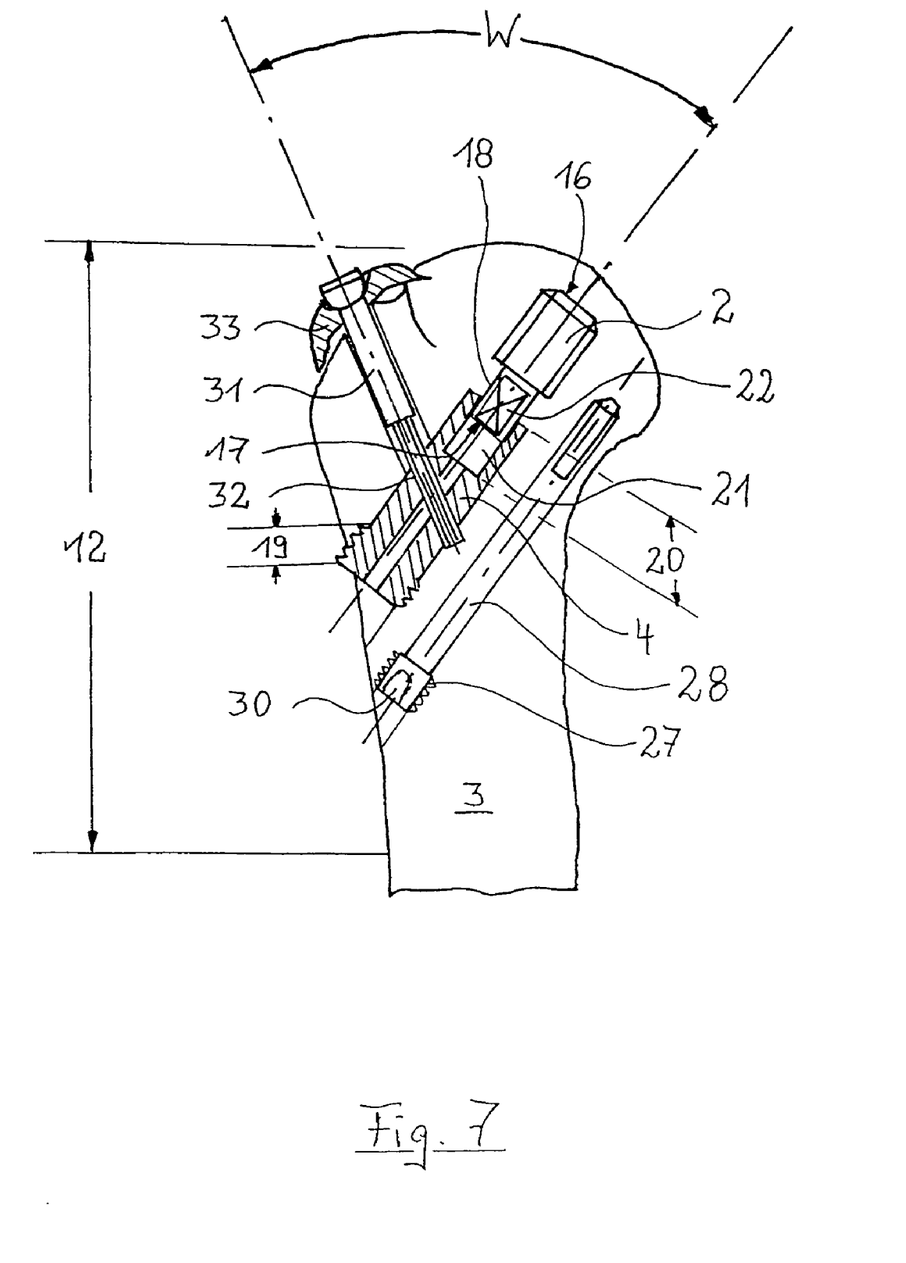
FIG. 7 is a sectional depiction of an inventive system in its installed position without an osteosynthetic plate.

FIG. 7 depicts the system as in FIG. 3 when installed, whereby the osteosynthetic plate has not been used because the cortical bone is strong enough.

Figure 8:
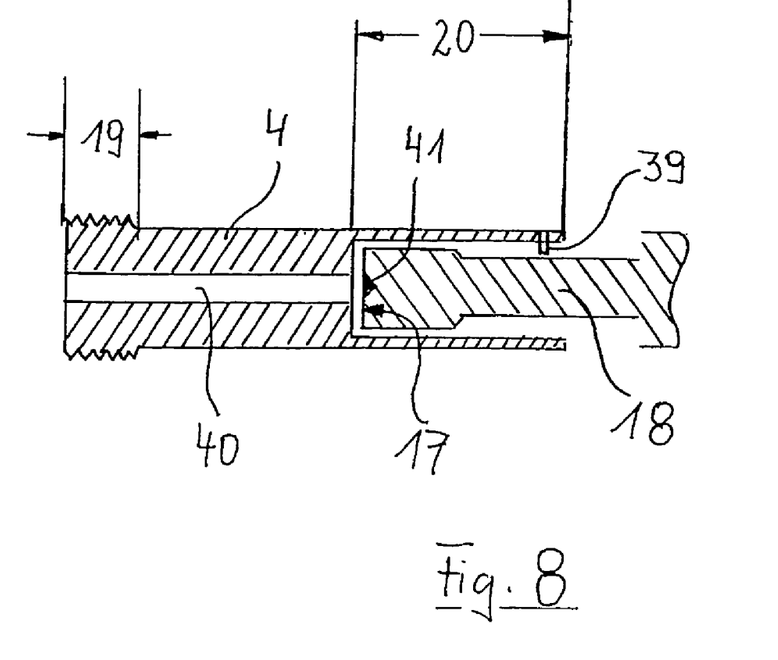
FIG. 8 is a sectional depiction of the connecting section with an interiorly positioned shaft of the fixation element.
Figure 9:
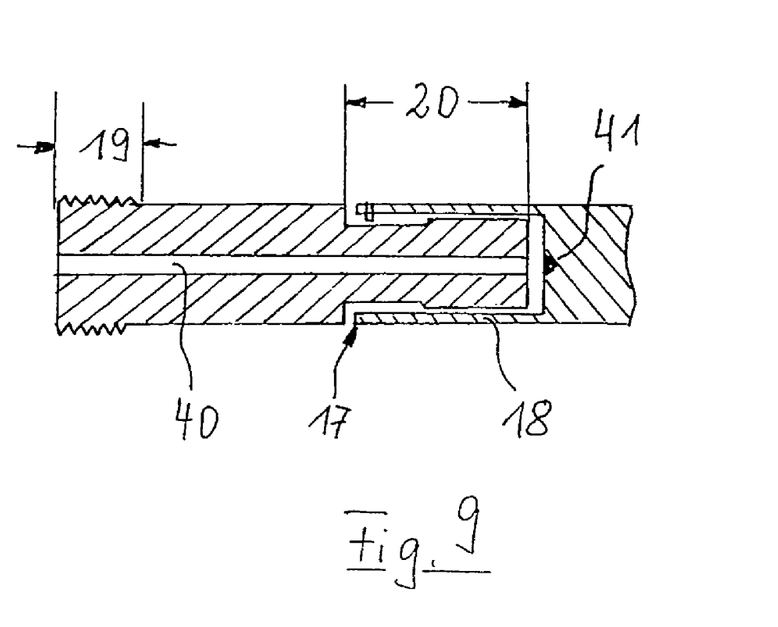
FIG. 9 is a sectional depiction of the connecting section with an exteriorly positioned shaft of the fixation element.

FIGS. 8 and 9 illustrate the connecting section between guide element 4 and fixation element 2. In FIG. 8, the shaft 18 is situated interior to the second connecting section 20 such that axial anti-tilt sliding is possible. The shaft 18 is prevented from sliding out of the second connecting section 20 in an undesired manner by the arranged limiting stop 39, in this case in the form of a pin that engages in a circumferential groove. In contrast to FIG. 8, in FIG. 9 the shaft 18 of the fixation element is arranged such that it exteriorly encloses the second connecting section 20 in an axially displaceable and anti-tilt manner. A limiting stop 39 is arranged in this case, as well. Thus the axial mobility can be set to a prespecified length.

A fixation recess 41 is arranged centrally at the back end of the fixation element 17 so that the fixation element 2, which can also be rotatably borne in or about the second connecting section 20. In this example it is a female thread into which a rotational tool (not shown) that can be conducted through the rotational tool bore 40 of the guide element 4 and that is screwed in and thus creates a nonpositive fit connection.

All of the elements in the inventive system that remain in the body comprise titanium or high quality steel. The target device 35 is made of wood or plastic in order to facilitate radioscopy.

The function and handling of the inventive system are explained in greater detail in the following using the procedure in a surgery for a subcapital humeral fracture.

After any required repositioning of the fracture fragments in a proximal humeral fracture, a small incision is made in the area of the upper arm below the humerus and the osteosynthetic plate 1 is inserted therethrough to the bone and then carefully urged upward along the bone 3, so that it scrapes the musculature. The target device 35 is already securely joined to the osteosynthetic plate 1. In this manner the osteosynthetic plate 1 is urged to the desired position until the support section 12 is adjacent to the fracture. Then the osteosynthetic plate 1 is fixed to the shaft of the bone 3 by means of the cortical bone screws 9, 10, 11. For this, a drill guided through the target bores 37 in the target device 35 is driven through the through-holes 6, 7, 8 into the shaft of the bone 3 and the corresponding cortical bone screws 9, 10, 11 are inserted into the bone. Initially the cortical bone screw 10 with the spherical head is mounted. The through-hole 7 embodied as an oblong hole then still makes it possible to correct the exact position of the osteosynthetic plate 1 relative to the bone 3 before the position of the osteosynthetic plate 1 is finally fixed by placing the cortical bone screws 9 and 11 into the through-holes 6 and 8.

Then the fracture can be temporarily fixed in that Kirschner wires are inserted through the bores 13 into the part of the bone 3 affected by the fracture. This temporary fixation is important in order in the next step to be able to add bores to the bone 3 through the first and second recesses 15, 29, which extend into the head fragment dislodged by the fracture. For this, again like for all of the other bores to be added to the bone 3 as well, the target bores 37 that are embodied in the target device 35 are used as a guide and are aligned with the corresponding recesses 15, 29 and through-holes 6, 7, 8 of the osteosynthetic plate 1.

After the bores have been created, the fixation element 2, using its self-cutting thread, is screwed into the bone fragment dislodged by the fracture and thereby fixed. It can be screwed in using a suitable tool, and this can even be accomplished by means of the guide element 4, which is joined with its second connecting section 20 to the fixation element 2. In any case, the guide element 4 is urged through the first recess 15 with a suitable tool and positioned such that it extends into the bone 3, the shaft 18 of the fixation element 2 is received in the seat 21, and the nose 24 is inserted into the groove 25. The guide element 4 is thus secured against undesired axial movement.

Somewhat below and parallel to the guide element 4, the anti-rotation screw 28 is placed using the target device 35 in order to fix the head fragment. The risk of undesired fracture movements during the surgery is reduced when the anti-rotation screw 28 having the smaller diameter is placed prior to the fixation element 2 having a larger diameter.

When required, for fixing the greater tuberosity fragment using the target device 35, an additional bore is added through this fragment diagonally from above (relative to the position of the bone illustrated in FIG. 3) into the bone 3. This is accomplished even before the guide element 4 is placed into the bone 3. After the guide element 4 has been positioned by rotating the nose 24 to the stop 34 such that the bore for the bone splinter fixation element 31 is aligned with the transverse bore 32, the bone splinter fixation element 31 is screwed into the transverse bore 32 and the greater tuberosity fragment is fixed in this manner.

The Kirschner wires that are for temporary fixation are then removed and where required replaced by screws that extend through the bores 13 and that with their heads are turned into the female thread embodied in the bores 13.

Finally the target device is detached at the clamping section 36 from the osteosynthetic plate 1 and removed therefrom. The osteosynthetic plate 1, the fixation element 2, the guide element 4, the anti-rotation screw 28, the bone splinter fixation element 31, and the cortical bone screws 9, 10, 11 remain in the body as implants until the fracture has healed completely.

If the cortical bone is adequately strong, the guide element 4 can be fastened to the fixation element 2 directly in the cortical bone of the bone 3. For preventing rotation of the fragment, at least one anti-rotation screw 28 can also be inserted directly in the fastening section.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

The invention claimed is:

1. A system for minimally invasive treatment of a fracture of a bone, comprising:
    an osteosynthetic plate including a support section positionable with a support surface against said bone adjacent to the fracture and a fastening section for fixing said osteosynthetic plate to said bone;
    a fixation element for fixing in a fragment of said bone that was dislodged by the fracture, and comprising a shaft portion;
    a guide element defining a longitudinal axis and including a first connecting section via which said guide element is fastenable to said osteosynthetic plate and a second connecting section for guiding said fixation element, said support section of said osteosynthetic plate having at least first and second recesses, said fixation element and said guide element being insertable into said bone through said first recess,
        said second connecting section and said shaft portion each comprising catch surfaces defining multiple sets of alternating straightened and curvilinear portions, when shown in cross-section, relative to a longitudinal axis of each of said second connecting portion and said shaft portion, said catch surfaces being relatively positioned so that said second connecting section defines a seat for said shaft portion, said second connecting section comprising a closed end portion and external seating surfaces defined by said second connecting section, and said catch surfaces of said shaft portion of said fixation element seat against so as to contact said external seating catch surfaces of said second connecting section so that said shaft portion is free from tilting and moveable axially with respect to said external seating surfaces of said second connecting section so as to be moveable axially toward and away from said closed end portion of said second connecting section, said relative positioning between said second connecting section and said shaft portion providing substantial alignment of said shaft portion along said longitudinal axis of said second connecting section for back and forth movement of said fixation element along said longitudinal axes of said second connecting section and said guide element during healing of the fracture, said movement and positioning providing a non-rigid connection between said guiding element and said fixation element,
    fastening structure for holding said guide element axially in place relative to said osteosynthetic plate, said fastening structure comprising a groove and a stop that are provided in said first recess of said support section, and a corresponding nose carried on said first connecting section of said guide element that is insertable into said groove, said nose being positionable against said stop to limit rotational movement of said guide element,
    an anti-rotation screw for substantially preventing rotation of the bone fragment, and comprising a head portion for insertion through said second recess of said support member and into said dislodged bone fragment, said head portion and said second recess being threaded for mating engagement therebetween, and
    a bone splinter fixation element fixable to and within said guide element for operatively securing a fragment of bone to said osteosynthetic plate.

2. A system according to claim 1, wherein said first recess in said support section and said guide element are configured such that a longitudinal axis of said guide element and a tangent on a side of said osteosynthetic plate facing said bone are at an angle of between 50° and 70°.

3. A system according to claim 1, wherein said first recess in said support section and said guide element are configured such that a longitudinal axis of said guide element and a tangent on a side of said osteosynthetic plate facing said bone are at an angle of between 55° and 65°.

4. A system according to claim 1, wherein said fastening structure includes a male thread provided on said first connecting section of said guide element and a female thread provided in said first recess which is engageable with the male thread.

5. A system according to claim 1, further comprising a bone splinter fixation element fixable in or to said guide element.

6. A system according to claim 1, wherein said guide element includes a transverse bore, and said bone splinter fixation element is fixable in said transverse bore.

7. A system according to claim 1, wherein said transverse bore is arranged in said guide element such that a longitudinal axis of said longitudinal bone splinter fixation element and a longitudinal axis of said guide element create an angle of between 60° and 100°.

8. A system according to claim 1, wherein said transverse bore is arranged in said guide element such that a longitudinal axis of said longitudinal bone splinter fixation element and a longitudinal axis of said guide element create an angle of between 70° and 90°.

9. A system according to claim 1, wherein said bone splinter fixation element includes a screw that has a pressure body with claws.

10. A system according to claim 1, wherein said at least a second recess has a female thread and said anti-rotation screw has a corresponding male thread at the head portion thereof.

11. A system according to claim 1, further comprising a target device that is detachable with said osteosynthetic plate via at least one clamping section.

12. A system according to claim 11, wherein said target device includes target bores that are aligned with the recesses in the osteosynthetic plate when said target device is connected to said osteosynthetic plate.

13. A system according to claim 1, wherein said fixation element includes a screw head with a self-cutting thread.

14. A system according to claim 1, wherein said fracture is a proximal humeral or femoral fracture.

15. A system for minimally invasive treatment of a fracture of a bone, comprising:
a support section receivable in a cortical bone of the bone, and comprising at least first and second recesses;
a fixation element for fixing in a fragment of said bone that was dislodged by the fracture, and comprising a shaft portion;
a guide element defining a longitudinal axis and including a first connecting section via which said guide element is fastenable in the cortical bone and a second connecting section for guiding said fixation element, said second connecting section of said guide element and said shaft of said fixation element being configured as anti-tilt and axially displaceable slides, said second connecting section and said shaft portion each comprising catch surfaces defining multiple sets of alternating straightened and curvilinear portions, when shown in cross-section, relative to a longitudinal axis of each of said second connecting portion and said shaft portion, said catch surfaces being relatively positioned so that said second connecting section defines a seat for said shaft portion, said second connecting section comprising a closed end portion and external seating surfaces defined by said second connecting section, and said catch surfaces of said shaft portion of said fixation element seat against so as to contact said external seating catch surfaces of said second connecting section so that said shaft portion is free from tilting and moveable axially with respect to said external seating surfaces of said second connecting section so as to be moveable axially toward and away from said closed end portion of said second connecting section, said relative positioning between said catch surfaces of said second connecting section and said shaft portion providing substantial alignment of said shaft portion along said longitudinal axis of said second connecting section for back and forth movement of said fixation element along said longitudinal axes of said second connecting section and said guide element during healing of the fracture, and said movement and positioning providing a non-rigid connection between said guiding element and said fixation element, fastening structure for holding said guide element axially in place relative to said osteosynthetic plate, said fastening structure comprising a groove and a stop that are provided in said first recess of said support section, and a corresponding nose carried on said first connecting section of said guide element that is insertable into said groove, said nose being positionable against said stop to limit rotational movement of said guide element, bone splinter fixation element fixable to and within said guide element for operatively securing a fragment of bone to said osteosynthetic plate, and at least one anti-rotation screw being arranged in said support section for preventing rotation of the bone fragment and which is placeable in the dislodged fragment of the bone, said screw comprising a head portion for insertion through said second recess of said support section and into said dislodged bone fragment, said head portion and said second recess being threaded for mating engagement therebetween.

16. A system according to claim 15, wherein said fracture is a proximal humeral or femoral fracture.

17. A system according to claim 15, wherein said second connecting section of said guide element and said shaft of said fixation element are configured as a slide such that said shaft of said fixation element is arranged in or about said second connecting section.

18. A system according to claim 15, wherein said fixation element with a thread on its forward end and said shaft is arranged anti-tilt and axially movable in or about said second connecting section as a slide bolt.

19. A system according to claim 15, wherein said shaft of said fixation element is movable in an axially limited manner in or about said second connecting section.

20. A system according to claim 15, wherein said support section and said guide element are configured such that a longitudinal axis of said guide element and a tangent to an outside of the cortical bone of the bone are at an angle of between 50° and 70°.

21. A system according to claim 15, wherein said support section and said guide element are configured such that a longitudinal axis of said guide element and a tangent to an outside of the cortical bone of the bone are at an angle of between 55° and 65°.

22. A system according to claim 15, wherein
said guide element includes a transverse bore; and
said bone splinter fixation element is fixable in said transverse bore.

23. A system according to claim 15, wherein a transverse bore is arranged in said guide element such that a longitudinal axis of said longitudinal bone splinter fixation element and the longitudinal axis of said guide element create an angle of between 60° and 100°.

24. A system according to claim 15, wherein a transverse bore is arranged in said guide element such that a longitudinal axis of said longitudinal bone splinter fixation element and a longitudinal axis of said guide element create an angle of between 70° and 90°.

25. A system according to claim 15, wherein said bone splinter fixation element is configured as a screw that has a pressure body with claws.

26. A system according to claim 15, wherein said guide element axially includes a rotational tool bore for receiving a rotational tool.

27. A system according to claim 15, wherein said fixation element includes a screw head with a self-cutting thread.

28. A system for minimally invasive treatment of a fracture of a bone, comprising:
an osteosynthetic plate including a support section positionable with a support surface against said bone adjacent to the fracture and a fastening section for fixing said osteosynthetic plate to said bone;
a fixation element defining a longitudinal axis for fixing in a fragment of said bone that was dislodged by the fracture, and comprising a shaft portion;
a guide element defining a longitudinal axis and including a first connecting section via which said guide element is fastenable to said osteosynthetic plate, a second connecting section for guiding said fixation element and a bore diagonally disposed relative to said first and second connecting sections, said support section of said osteosynthetic plate having at least first and second recesses, said fixation element and said guide element being insertable into said bone through said first recess,
said second connecting section and said shaft portion being relatively positioned so that said second connecting section and shaft portion are each aligned along their respective longitudinal axes, said second connecting section defining a seat for said shaft portion, said second connecting section comprising a closed end portion and a circumferential seating surface, and said shaft portion being seatable against so as to contact said circumferential seating surface so that said shaft portion is free from tilting and moveable axially with respect to said circumferential seating surface of said second connecting section so as to be moveable axially toward and away from said closed end portion of said second connecting section while each of said second connecting section and said shaft portion are freely rotatable relative to each other when aligned along their respective longitudinal axes, said relative positioning between said second connecting section and said shaft portion providing substantial alignment of said shaft portion along said longitudinal axis of said second connecting section for back and forth movement of said fixation element along said longitudinal axes of said second connecting section and said guide element during healing of the fracture, said movement and relative positioning providing a non-rigid connection between said guiding element and said fixation element;

fastening structure for holding said guide element axially in place relative to said osteosynthetic plate;

an anti-rotation screw for substantially preventing rotation of the bone fragment, and comprising a head portion for insertion through said second recess of said support member and into said dislodged bone fragment, said head portion and said second recess being threaded for mating engagement therebetween, and a bone splinter fixation element that is fixable to and within said guide element for securing a fragment of bone relative to said osteosynthetic plate, said bone splinter fixation element being diagonally disposed to said longitudinal axis of said guide element, said guide element being freely rotatable about said shaft portion of said second connecting section so as to be adjustable with respect to said fixation element, said free rotation of said guide element enabling adjustment of said bore of said guide element so as to position said guide element for receipt of said bone splinter fixation element within said bore of said guide element.

29. A system according to claim 28, wherein said fastening structure comprises a groove and a stop that are provided in said first recess of said support section, and a corresponding nose carried on said first connecting section of said guide element that is insertable into said groove, said nose being positionable against said stop to limit rotational movement of said guide element.

30. A system according to claim 28, wherein said fastening structure comprises matingly engageable threads on each of the guide element and the osteosynthetic plate.

* * * * *